(12) United States Patent  (10) Patent No.: US 8,151,645 B2
Vivek et al.  (45) Date of Patent: Apr. 10, 2012

(54) METHODS AND APPARATUS FOR ULTRASONIC COUPLING USING MICRO SURFACE TENSION AND CAPILLARY EFFECTS

(75) Inventors: Vibhu Vivek, Santa Clara, CA (US); Antonio Lucero, Fresno, CA (US); Michael Travis, SuiSun City, CA (US)

(73) Assignee: Microsoft Systems Inc., San Jose, CA (US)

( * ) Notice: Subject to any disclaimer, the term of this patent is extended or adjusted under 35 U.S.C. 154(b) by 564 days.

(21) Appl. No.: 12/418,505

(22) Filed: Apr. 3, 2009

(65) Prior Publication Data

US 2009/0249866 A1 Oct. 8, 2009

Related U.S. Application Data

(60) Provisional application No. 61/042,568, filed on Apr. 4, 2008.

(51) Int. Cl.
*G01N 24/00* (2006.01)
(52) U.S. Cl. ......................................................... 73/644
(58) Field of Classification Search ...................... 73/644
See application file for complete search history.

(56) References Cited

U.S. PATENT DOCUMENTS

| | | | |
|---|---|---|---|
| 3,798,961 A * | 3/1974 | Flambard et al. | 73/644 |
| 3,934,460 A | 1/1976 | Sherwin et al. | |
| 4,033,178 A | 7/1977 | Holt et al. | |
| 4,472,975 A * | 9/1984 | Beck et al. | 73/644 |
| 5,041,849 A | 8/1991 | Quate et al. | |
| 5,278,028 A | 1/1994 | Hadimioglu et al. | |
| 5,469,744 A | 11/1995 | Patton et al. | |
| 5,669,971 A | 9/1997 | Bok et al. | |
| 5,983,723 A | 11/1999 | Buckin et al. | |
| 6,364,454 B1 | 4/2002 | Hadimioglu | |
| 6,368,482 B1 | 4/2002 | Oeftering et al. | |
| 6,666,541 B2 | 12/2003 | Ellson | |
| 6,682,214 B1 | 1/2004 | Vivek et al. | |
| 6,948,843 B2 | 9/2005 | Laugharn, Jr. et al. | |
| 7,080,557 B2 | 7/2006 | Adnan | |

(Continued)

FOREIGN PATENT DOCUMENTS

WO WO-2009124289 A2 10/2009

(Continued)

OTHER PUBLICATIONS

"International Application Serial No. PCT/US2009/039546, Search Report mailed Jul. 8, 2009", 3 pgs.

(Continued)

*Primary Examiner* — Hezron E Williams
*Assistant Examiner* — Nathaniel Kolb
(74) *Attorney, Agent, or Firm* — Schwegman, Lundberg & Woessner, P.A.

(57) ABSTRACT

Apparatus and methods for ultrasonic coupling between a coupling fluid and an object using micro surface tension and capillary effects are provided. The apparatus may include a chamber comprising a wall, a bottom, and a fluid inlet. The fluid inlet may allow a fluid to enter the chamber. Portions of the wall may have a number of slits with dimensions that allow a controlled overflow of the fluid to hold a top surface of the fluid in a stable contact with the object when the fluid is flowing into the chamber. The object may be located at a distance from the top of the wall. Additional apparatus and methods are disclosed.

29 Claims, 7 Drawing Sheets

U.S. PATENT DOCUMENTS

| | | | |
|---|---|---|---|
| 7,100,449 B2* | 9/2006 | Busch et al. | 73/644 |
| 7,530,271 B2* | 5/2009 | Busch et al. | 73/644 |
| 7,628,075 B2* | 12/2009 | Kennedy et al. | 73/628 |
| 2005/0061078 A1 | 3/2005 | Miller et al. | |
| 2007/0012115 A1* | 1/2007 | Busch et al. | 73/644 |
| 2007/0227250 A1* | 10/2007 | Kennedy et al. | 73/641 |
| 2009/0249877 A1 | 10/2009 | Vivek | |
| 2009/0254289 A1 | 10/2009 | Vivek et al. | |

FOREIGN PATENT DOCUMENTS

| | | | |
|---|---|---|---|
| WO | WO-2009124290 A1 | 10/2009 | |

OTHER PUBLICATIONS

"International Application Serial No. PCT/US2009/039546, Written Opinion mailed Jul. 8, 2009", 6 pgs.

Ellson, Richard, et al., "Transfer of low nanoliter volumes between microplates using focused acoustics—automation considerations", *Journal of the Association for Laboratory Automation*, 8(5), (Oct. 2003), 29-34.

Elrod, S. A, et al., "Nozzleless droplet formation with focused acoustic beams", *J. Appl. Phys. 65*, (1989), 3441-3447.

Farnow, S. A, "Aocustic Applications of the Zone Plate", *Ph.D Dissertation, Stanford University*, (1976), 152 pgs.

Hadimioglu, B., et al., "Acoustic ink printing", *IEEE Ultrasonics Symposium, 1992. Proceedings*, (1992), 929-935.

Hadimioglu, B., et al., "Acoustic ink printing: an application of ultrasonics for photographic quality printing at high speed", *2001 IEEE Ultrasonics Symposium*, (2001), 627-635.

Hadimioglu, B., et al., "High-efficiency Fresnel acoustic lenses", *IEEE Ultrasonics Symposium, 1993. Proceedings*, (1993), 579-582.

Oeftering, R. C, "Improving plating by use of intense acoustic beams", *NASA Tech Briefs*, (Mar. 2003), 2 pgs.

Vivek, V., et al., "Novel acoustic-wave micromixer", *Proc. IEEE Int. Micro Electro Mechanical Syst. Conf.*, (2000), 668-673.

Zou, Q., et al., "Water Needle— A new phenomenon for ink-jet printing", *IEEE 2001 International Conference on Solid-State Sensors and Actuators*, (2001), 6 pgs.

* cited by examiner

SIDE VIEW

TOP VIEW

US 8,151,645 B2

METHODS AND APPARATUS FOR ULTRASONIC COUPLING USING MICRO SURFACE TENSION AND CAPILLARY EFFECTS

RELATED APPLICATIONS

This patent application claims the benefit of priority under 35 U.S.C. Section 119(e), to U.S. Provisional Patent Application Ser. No. 61/042,568, filed on Apr. 4, 2008, which is incorporated herein by reference in its entirety.

BACKGROUND

Devices utilizing ultrasonic waves at megahertz (MHz) frequencies are used in many applications such as ultrasonic non-destructive evaluation of sample materials, ultrasonic imaging, ultrasonic ink printing, ultrasonic mixing, droplet dispensing for pharmaceutical and biological applications, and selective coating or plating of materials on substrates.

In virtually all of the above-mentioned applications, the core of the system consists of an ultrasonic transducer that converts electrical signals into ultrasonic signals and vice versa. The ultrasonic transducer is typically a piezoelectric plate formed between two metal electrodes. Other forms of ultrasonic transducers are also known in the art and may be used in various applications of ultrasonic energy.

BRIEF DESCRIPTION OF THE DRAWINGS

Some embodiments of the disclosed technology are illustrated by way of example and not limitation in the figures of the accompanying drawings in which.

DETAILED DESCRIPTION

Figure 1:
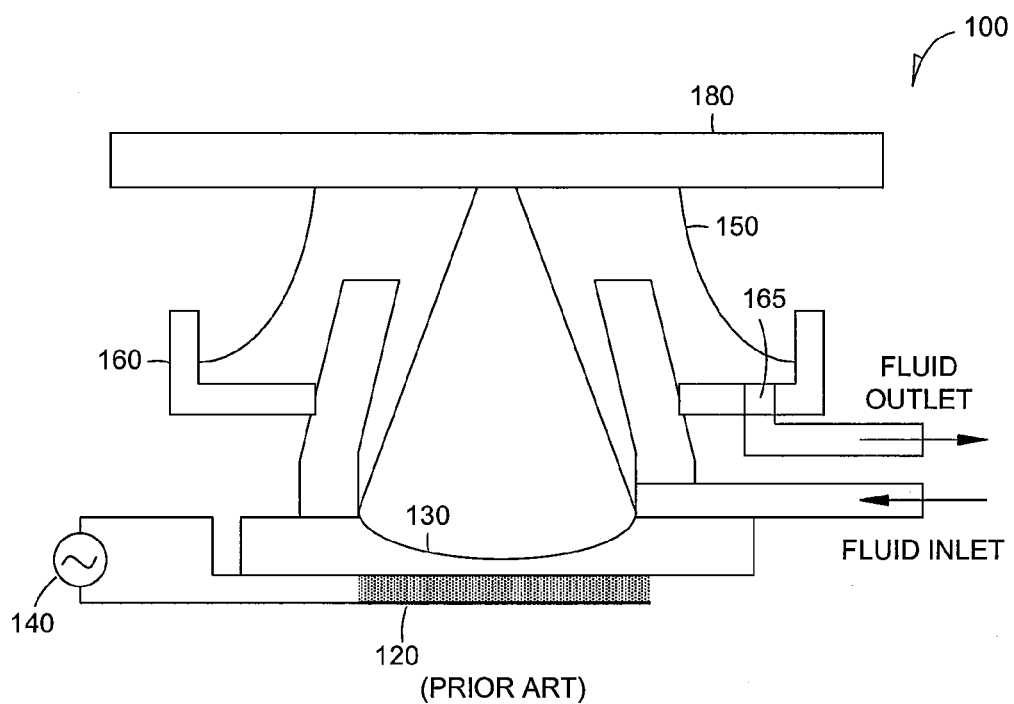
FIG. 1 is a diagram illustrating a cross-section of a prior art ultrasonic device known as bubbler.

Example apparatus and methods for ultrasonic coupling between a coupling fluid and an object using micro surface tension and capillary effects will be described. In the following description for the purpose of explanation, numerous examples having example-specific details are set forth to provide an understanding of example embodiments. It will be evident, however, to one skilled in the art that the present examples may be practiced without these example-specific details, and/or with different combinations of the details than are given here.

Some example embodiments described herein may include an apparatus including a chamber, a wall, a bottom, and a fluid inlet. The fluid inlet may allow a fluid to enter the chamber. Portions of the wall may have a number of slits, apertures, openings, or holes with dimensions that allow a controlled overflow of the fluid to hold a top surface of the fluid in a stable contact with an object when the fluid is flowing into the chamber. The object may be located at a distance from the top of the wall. The chamber may comprise a rectangular cylinder, and a slits portion of the wall may include at least one side of the rectangular cylinder. The slits may have similar or dissimilar dimensions, and the dimensions of each slit may include a width and a height.

In example embodiments the width and/or the height of one or more of the slits may provide sufficient surface tension to keep the fluid from escaping the chamber before the top surface of the fluid contacts the object. The contacted area of the top surface of the fluid with the object may be controlled by adjusting the width and/or the height of one or more of the slits. The object may be a well plate including one or more wells that can retain liquid samples. The bottom may include an ultrasonic transducer array formed by a sensor plate and a number of electrodes. The electrodes may be conductively coupled to a radio frequency (RF) source.

The RF source may, for example, generate RF signals in the form of impulse or signals with tone-burst waveforms. The frequency of the RF signals may be adjusted by sweeping an operating frequency of the RF signals across a frequency range (e.g., 0.1-1000 MHz). The signals may be suitably amplified, and they may then be applied between the electrodes of the ultrasonic transducer (also referred to, hereinafter, as a "transducer"). The transducer may convert the electrical energy of the RF signal into ultrasonic energy in the form of ultrasonic waves that are directed towards one or more samples. Depending on the application and particular design, the transducer may be attached to a buffer plate on one side, typically towards the object (e.g., a micro-well plate, or simply a "well plate"), and to a backing material on the opposing side. Again, depending on the application, a suitable ultrasonic converging element (also known as an ultrasonic lens, hereinafter called a "converging element") may be formed on the transducer to locally converge the ultrasonic energy over a selected area of a sample object that retains a sample.

The form of the sample object depends on the particular application. In applications such as non-destructive evaluation or ultrasonic imaging, it is typically a solid material that may be examined by the ultrasonic signals. In fluidic applications such as mixing, the sample object is typically an industry-standard micro-well plate that holds the sample, e.g., fluid solvents that will be agitated by the ultrasonic signals. The micro-well plate typically has a relatively thin bottom to allow for efficient transmission of the ultrasonic waves into the sample. The fluid solvents may also contain particulates or solids to be mixed as well. In yet other biological applications, the samples may be placed on glass slides.

In virtually all of the applications described above, the sample object may be free to move, because the sample object is scanned relative to the transducer (e.g., in imaging applications), or in fluidic applications, it may be brought in and out of the instrument quickly, once the desired function (e.g., mixing or fluid transfer) is accomplished. The sample object is typically placed from a few millimeters to several centimeters away from the transducer assembly, near the zone where the ultrasonic energy may be concentrated.

Because air and virtually all gases do not transmit ultrasonic waves at megahertz frequencies efficiently, a medium (e.g., a coupling fluid, typically water) is applied between the transducer and the sample object to couple the ultrasonic energy (e.g., ultrasonic waves) efficiently between the transducer and the sample. In some of the applications described herein, it is usually not desired to immerse all of the transducer and sample assemblies into the coupling fluid. In order to provide reliable liquid contact between the transducer and the sample object such that the contact would not be lost over time due to the evaporation of the coupling fluid, a mechanism that continuously replenishes the coupling fluid between the transducer and the sample object may be used. Such assemblies are commonly referred to as "bubbler" assemblies (see, for example, Olympus NDT Inc., immersion transducer catalog).

The bubbler mechanisms commonly used in many ultrasonic applications may have several potentially undesirable attributes. They use a mechanical pump to re-circulate the coupling fluid, which adds further cost and complexity to the instrument. In addition, the pump is a potential source of instrument failure. The relatively high flow rate of the coupling fluid is a potential source of overflows and resultant catastrophic failures. Most biological applications use a micro-well plate with a plurality of micro-wells to retain sample fluids and a transducer to generate ultrasonic energy that can process the sample fluids. The spacing between the micro-well plate and a transducer can be very small, from less than a millimeter to about 25 millimeters. The traditional bubbler assemblies, as discussed below, may not be particularly suitable for such applications.

FIG. 1 is a diagram illustrating a cross-section of a prior art ultrasonic device 100 known as bubbler. The cross-section shown in FIG. 1 is made through the fluid inlet and outlet. The ultrasonic transducer 120 excited by an RF source 140 may generate ultrasonic energy in the form of ultrasonic waves that are focused using a converging element 130. The ultrasonic energy is coupled to the object 180 via a coupling fluid 150. The coupling fluid 150 is forced or otherwise introduced or supplied into a reservoir via a mechanical pump. The coupling fluid may exit the reservoir through the outlet 165. By adjusting a balance between the input and output flow, the coupling fluid is kept in contact with the object 180.

For biological applications, a "low-profile" structure to fill in the small gap between the micro-well plate and the transducer, while satisfying the mechanical limitations of the system, may be used. However, in typical bubbler assemblies such as the ultrasonic device 100, it may not be possible to precisely control a contact area of coupling fluid 150 and the object 180. The contact area may spread over parts of the sample that may not be desired to wet with the coupling fluid (as removing the coupling fluid may involve extensive drying operations). For example, the micro-well plates for biological applications mentioned herein are particularly susceptible to the issue of removing the coupling fluid after the desired operation is completed. In conventional bubbler systems, the coupling fluid tends to be trapped in the "skirt" area of the micro-well plate.

There is also a possibility of having trapped air bubbles that prevent efficient transfer of ultrasonic energy between the transducer and the sample. In addition, in some biological applications, it may be desired to use micro-well plates that have a non-flat bottom to reduce the "dead" volume of liquid. When such plates are used with current bubbler assemblies, it may not be practical or possible to achieve good contact with the non-flat bottom to provide efficient coupling of ultrasonic energy. Non-flat bottom plates are typically more prone to trapped air bubbles.

Figure 2:
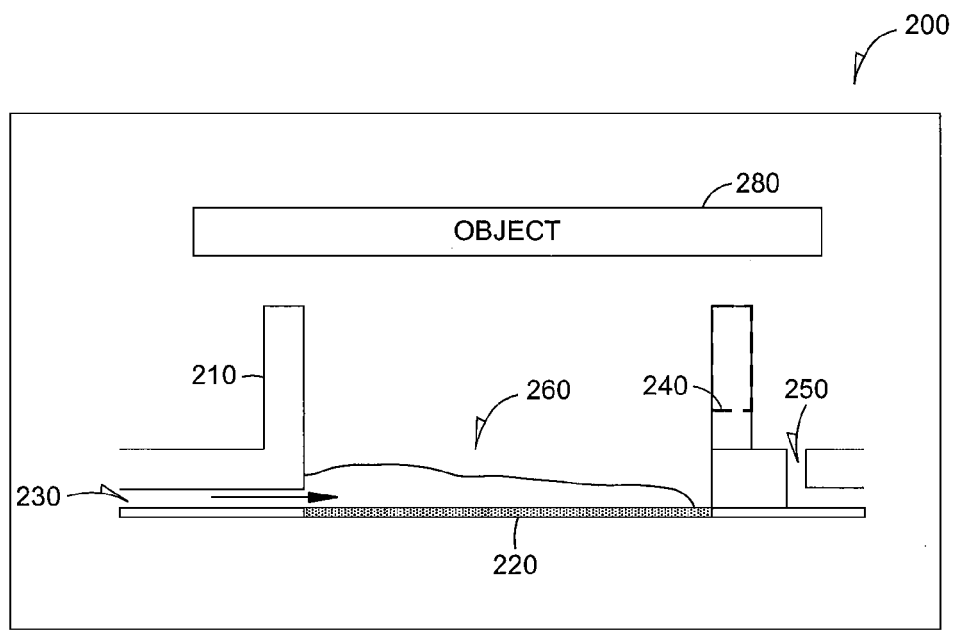
FIG. 2 is a diagram illustrating a cross-section of an example apparatus for ultrasonic coupling using micro surface tension and capillary effects, according to various embodiments of the invention.
Figure 6:
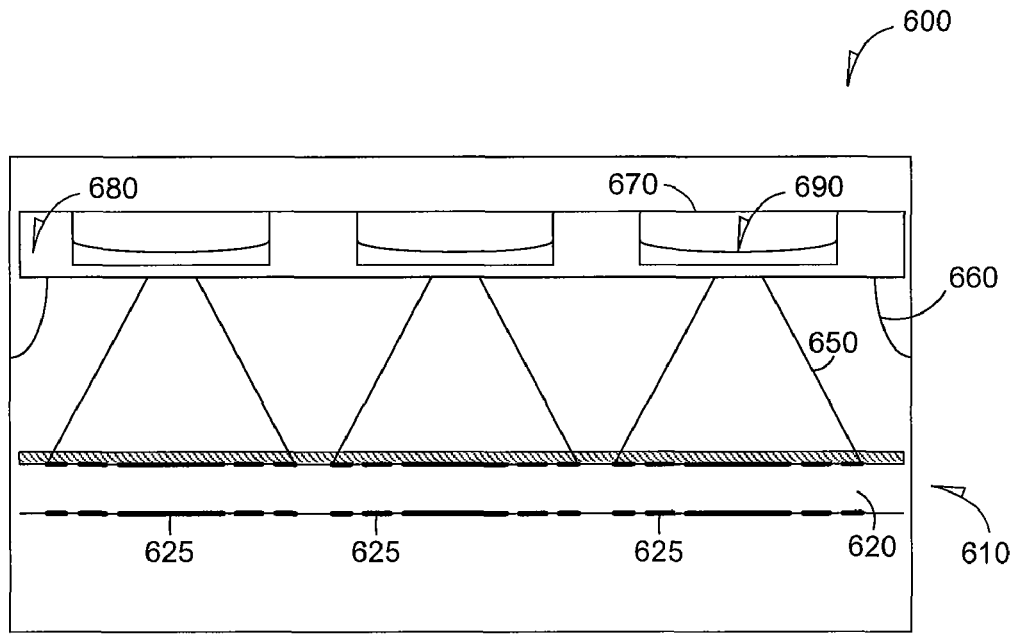
FIG. 6 is a diagram illustrating an example apparatus for ultrasonic coupling of a coupling fluid with a micro-well plate using micro surface tension and capillary effects, according to various embodiments of the invention.

Example embodiments disclosed in the present disclosure will address potential problems that may not be solved by employing bubbler assemblies, for example, in ultrasonic applications. In the example embodiments described in this document, the coupling fluid is held within a chamber that allows the coupling fluid to contact both the transducer array and the bottom of the sample using micro surface tension and capillary effects FIG. 2 is a diagram illustrating a cross-section of an example apparatus 200 for ultrasonic coupling using micro surface tension and capillary effects, according to various embodiments of the invention. A coupling fluid 260 may be pumped into a reservoir via an inlet 230. The level of the coupling fluid 260 may rise within the chamber 210. The chamber 210 may comprise slits 240 on certain portions of its wall such as on one or more sides of the chamber 210. In example embodiments, the slits may be formed all around the chamber, and in other embodiments they may be formed only in selected regions of the chamber periphery. The chamber 210 may have the form of a rectangular cylinder. Other geometrical shapes for the chamber 210 may also be acceptable. The level of the coupling fluid 260 may rise to contact an object 280 to allow the ultrasonic waves generated by an ultrasonic transducer 220 to couple to the object 280. An outlet 250 may permit excess coupling fluid 260 to exit the chamber 210. The object 280 may include a micro-well plate 680 comprising a number of micro-wells 670 as shown in FIG. 6.

Figure 3:
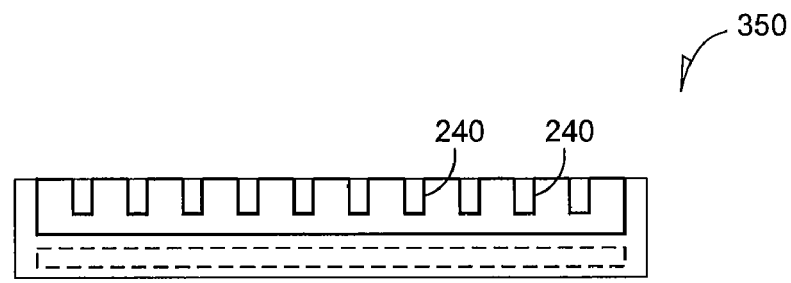
FIG. 3 is a diagram illustrating views of the example apparatus of FIG. 2, according to various embodiments of the invention.
Figure 3:
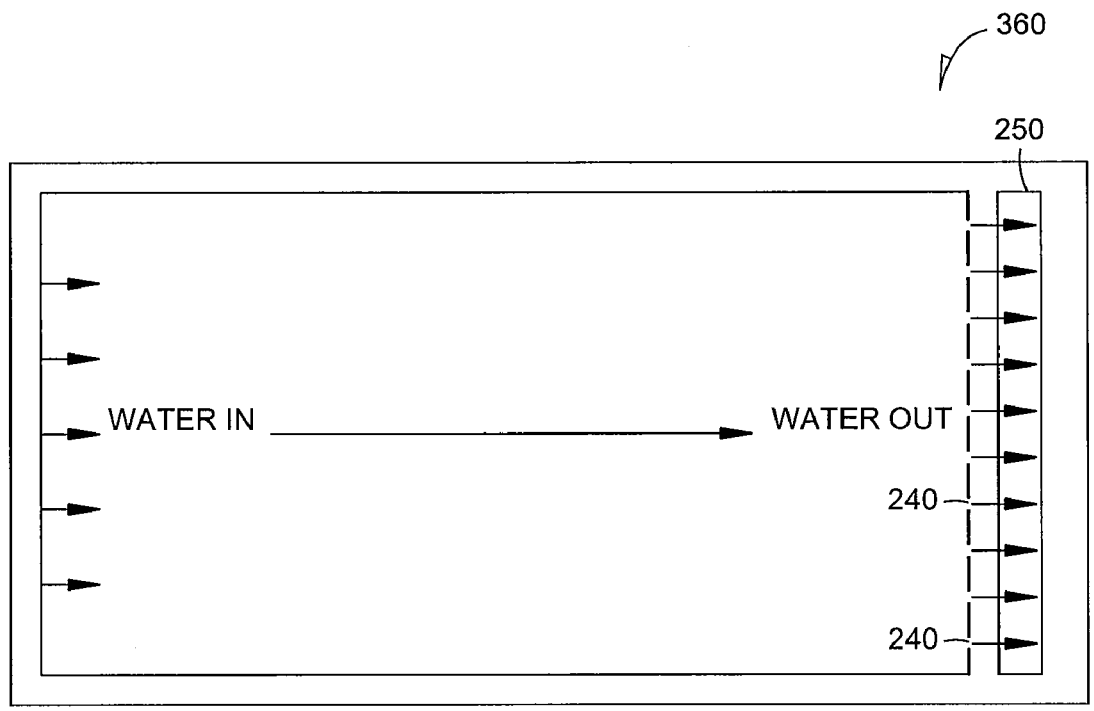

FIG. 3 is a diagram illustrating views of the example apparatus 200 of FIG. 2, according to various embodiments of the invention. A side view 350 of the chamber 210 (FIG. 2) shows an example configuration of the slits 240. FIG. 3 also shows a top view 360 of the chamber 210. The top view 360 illustrates how the coupling fluid (e.g., water) may exit from the top of the slits 240 and be collected through the outlet 250. Although the slits 240 are shown to be rectangular, in example embodiments, they may have other shapes and/or may include tapering. The tapering may be from in-to-out or from out-to-in, flat or non-flat. The dimensions (e.g., a width and a height) of the slits 240 may vary depending on the location of each slit. The slits 240 may comprise one or more layers of some material that may influence surface tension. The material may be applied to the slits by coating or other suitable operation.

Figure 4:
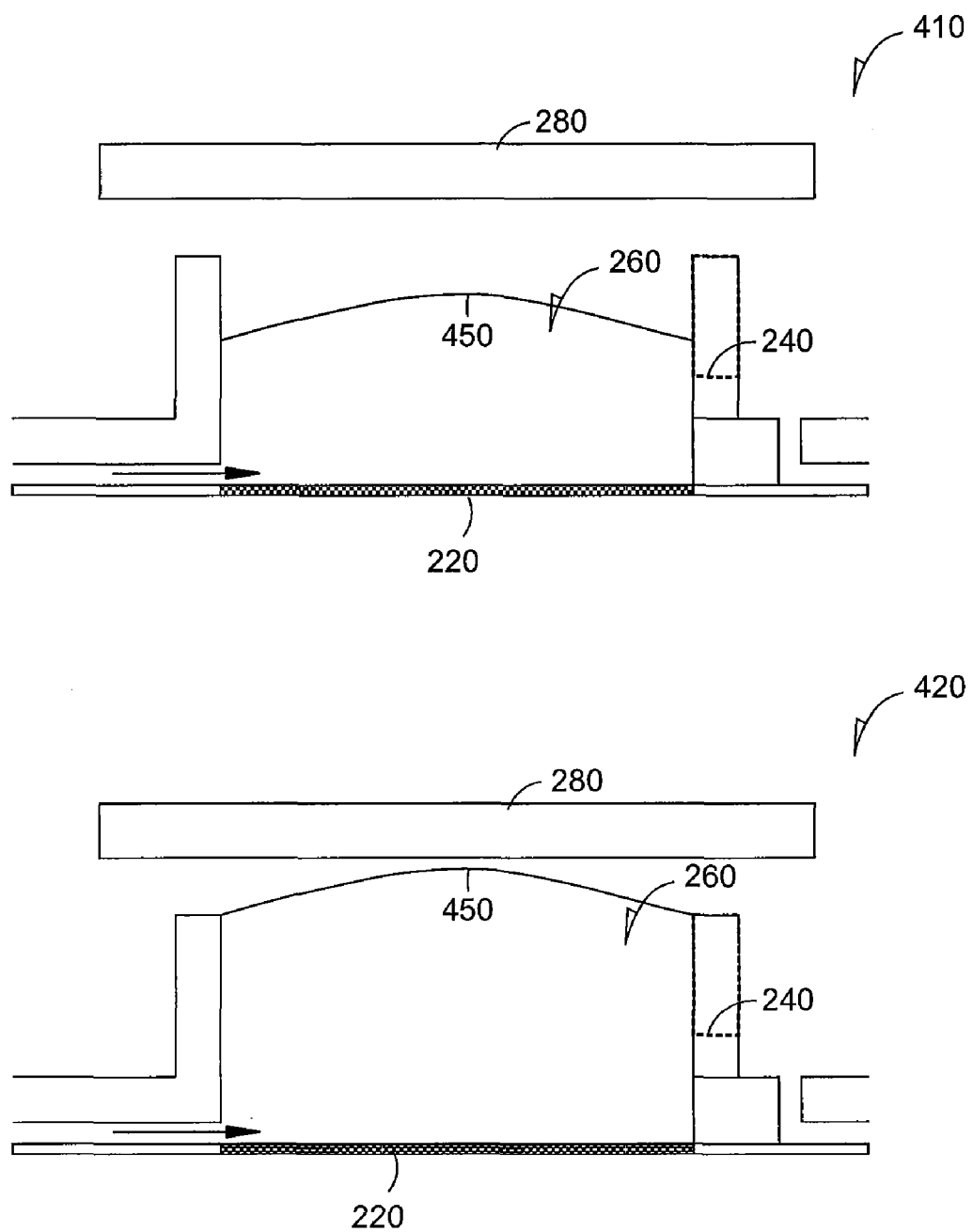
FIG. 4 is a diagram illustrating example operation modes of the apparatus of FIG. 2, when a fluid mound is rising, according to various embodiments of the invention.

FIG. 4 is a diagram illustrating example operation modes of the apparatus 200 of FIG. 2, when a fluid mound is rising, according to various embodiments of the invention. In an example operation mode 410, the coupling fluid 260 has risen to a level 450, which is above the lower end of the slits 240. However, at this point there is no leaking of the coupling fluid from the slits 240. In fact the coupling fluid 260 is held back by the surface tension and capillary effects created between the coupling fluid 260 and the slits 240. This will allow a volume of coupling fluid 260 to collect and the level 450 of the coupling fluid 260 to continue to rise as seen in an example operation mode 420. The coupling fluid 260 may continue to rise until reaching the bottom of the sample (see, for example, FIG. 5). It is to be noted that at this point of operation of the apparatus 200, as shown by the operation modes 410 and 420, no RF pulse is yet applied to the ultrasonic transducer 220. Once the coupling fluid 260 contacts the object 280, two things may happen, as discussed below regarding FIG. 5.

Figure 5:
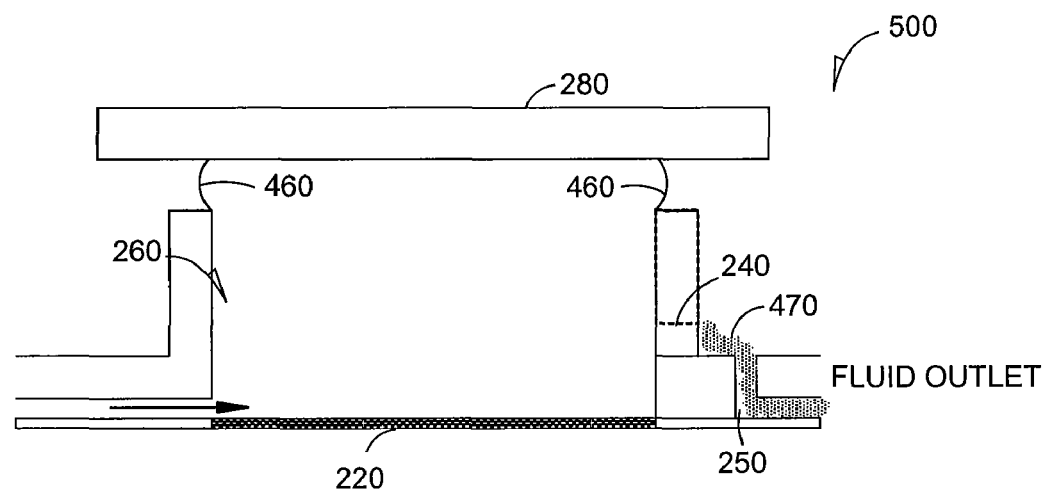
FIG. 5 is a diagram illustrating an example operation mode of the apparatus of FIG. 2, when a fluid mound is brought into contact with the object, according to various embodiments of the invention.

FIG. 5 is a diagram illustrating an example operation mode 500 of the apparatus of FIG. 2, when a fluid mound is brought into contact with the object 280, according to various embodiments of the invention. When the contact between the coupling fluid 260 and the object 280 is formed, first the fluid will cling to the sample, thus producing an air-free environment. Second, once bulges 460 start to form, the fluid surface tension that was holding the coupling fluid 260 back from escaping through the slits 240 may break and allow coupling fluid 260 to flow through the slits 240 into the outlet 250 and back out into the system (see, for example, overflow 470).

The slits 240 may allow for a reservoir of coupling fluid 260 to be created, while at the same time allowing excess coupling fluid 260 to leave the system. By using such a design, we are able to apply coupling fluid only to desired sections of the object 280. Finally, this reservoir may provide an air-free environment that allows the ultrasonic transducer array 220 to achieve desired efficiency for ultrasonic energy transfer between the ultrasonic transducer array 220 and the object 280. In addition, the coupling fluid 260 has the opportunity to drain in a manner that allows for decoupling of the coupling fluid 260 from the object 280. A series of drains combined with a vacuum source may allow for a quick reduction of the coupling fluid 260 from the chamber 210 (FIG. 2). This may provide quicker removal times as well as a reduction in the amount of coupling fluid 260 that stays on the object 280.

The apparatus 200 of FIG. 2 may also contain features to replenish the coupling fluid 260 to keep its surface near a predetermined level, as the coupling fluid 260 may be lost due to evaporation over time. Due to the effective coupling and low-profile design that permits the ultrasonic waves to couple directly into the sample, the apparatus 200 may be capable of operating with a low-energy RF pulse to the ultrasonic transducer 220.

Using the example method described above regarding FIGS. 4 and 5 to provide coupling between the ultrasonic transducer 220 and the object 280, it may be possible to obtain a larger contact area of coupling fluid 260 and the object 280, unlike the conventional bubblers used in the current state of art. It may also be possible to avoid wetting of the parts of the object 280 that are not desired to have liquid contact. Once the coupling fluid 260 makes contact with the object 280, the coupling fluid may maintain contact with the object 280 or it may take a period of time for the coupling fluid 260 to break contact with the object 280, even after the pump is turned off, due to the capillary forces between the object 280 and the coupling fluid 260.

While the coupling fluid 260 is still in contact with the object 280, it is possible to excite the ultrasonic transducer 220 by applying an RF signal to the ultrasonic transducer 220. The RF signal may include an impulse and/or signals having tone-burst waveforms (depending on the particular application). The application of a certain type of RF signal may depend on the desired functionality of the apparatus 200. For example different RF signals may be applied when the apparatus 200 is used in ultrasonic imaging (e.g., for examining sample surfaces) or in liquid sample mixing applications where liquid samples held in wells of a micro-well plate are mixed. If desired (e.g., if the contact is lost after a certain period of time), the mechanical pump may be turned on continuously or intermittently to provide long-term contact of the coupling fluid 260 with the object 280.

The described example embodiments provide significant potential benefits in instruments that operate with an array of transducers and converging elements, typically used in biological or pharmaceutical applications that involve liquid manipulation over a multitude of fluid samples using focused ultrasonic energy. Some examples of such devices and their applications are described in the concurrently submitted patent application entitled "Methods and Systems to Form High Efficiency and Uniform Fresnel Lens Arrays for Acoustic Liquid Manipulation."

FIG. 6 is a diagram illustrating an example apparatus 600 for ultrasonic coupling of a coupling fluid with a micro-well plate using micro surface tension and capillary effects, according to various embodiments of the invention. The apparatus 600 includes an ultrasonic transducer array 610 formed by configuring a number of ultrasonic converging elements 625 on the top and bottom sides of a sensor plate (e.g., piezoelectric material) 620. Top and bottom electrodes may be configured to have solid shapes (e.g., uniform, continuous, and free from any cut within their boundaries) or patterned to form Fresnel-type lenses. The pattern may include concentric rings forming a sector with a central angle. The central angle may assume different values such as 45, 90, and 135 degrees, etc.

The fluid samples 690 to be manipulated are contained in micro-wells 670 of a micro-well plate 680, which may be held (by means not shown in the drawing) near the nominal focal distance (e.g., a distance from a transducer where the ultrasonic waves generated by that transducer converge) of the ultrasonic transducer array 610. The sheet of coupling fluid 660 can be dynamic (e.g., continuously moving and re-circulating) or static, possibly being replenished only as the coupling fluid 660 evaporates. Therefore, using a chamber with slits and utilizing the operation modes described above, it may be possible to make fluidic contact with the bottom of the micro-well plate 680 and keep the rest of the plate (e.g., skirt of plate) dry to make it significantly easier to perform plate-drying operations.

It is also possible to use example embodiments of the present inventive subject matter in conjunction with a structure described in the concurrently submitted patent application entitled "Methods and Apparatus for Ultrasonic Using Ultrasonic Radiation Pressure," (incorporated herein by reference in its entirety) both to fill in the area between the ultrasonic transducer array 610 and the micro-well plate 680 with the coupling fluid 660 and to reduce the possibility of bubbles interfering with good ultrasonic coupling. The bubbles formed in the coupling fluid 660 may be detected and dislodged by tuning the radio frequency source (e.g., the RF source 140). Such usage can be particularly important in those biological applications where micro-well plates that have a non-flat bottom are employed to reduce the "dead" volume of liquid.

Figure 7:
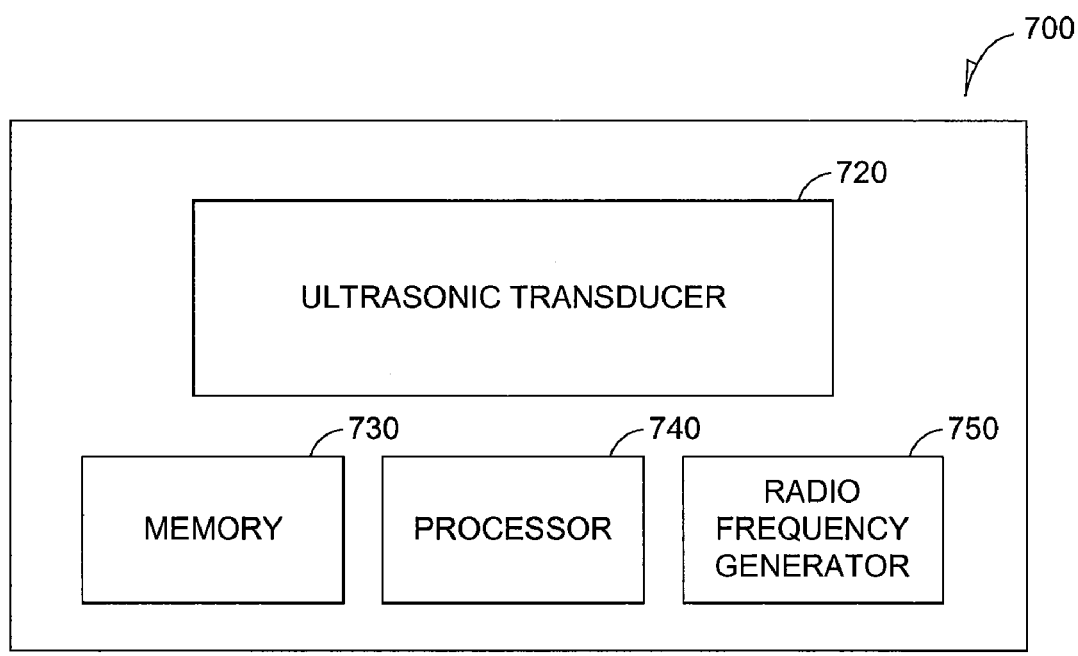
FIG. 7 is a diagram illustrating an example system for ultrasonic coupling using micro surface tension and capillary effects, according to various embodiments of the invention.

FIG. 7 is a diagram illustrating an example system 700 for ultrasonic coupling using micro surface tension and capillary effects, according to various embodiments of the invention. The system 700 may include an ultrasonic transducer 720, memory 730, a processor 740, and a radio frequency generator 750 (such as the RF source 140 of FIG. 1). Example embodiments of the ultrasonic transducer 720 may include ultrasonic transducers 220 and 610 shown in FIGS. 2 and 6. However, the ultrasonic transducer 720 may not be limited to parts and components shown in the above-mentioned figures and may include auxiliary components not shown in those figures.

In example embodiments, the system 700 may use the processor 740 to execute instructions (e.g., software) stored in the memory 730. The processor 740 may include a microprocessor, a central processing unit (CPU), and/or the like. The memory 730 may be rotating memory, random access memory (RAM), read-only memory (ROM), or flash type memory. The memory 730 may also store data related to the operation of the system 700, for example, maintenance data, data related to samples analyzed, etc. The instructions, for example, may include software to control various parts of the system 700 such as the radio frequency generator 750 and/or one or more pumps that may propel a coupling fluid (such as a coupling fluid 260 of FIG. 2) into the chamber 210 of FIG. 2 that contains the coupling fluid 260.

Figure 8:
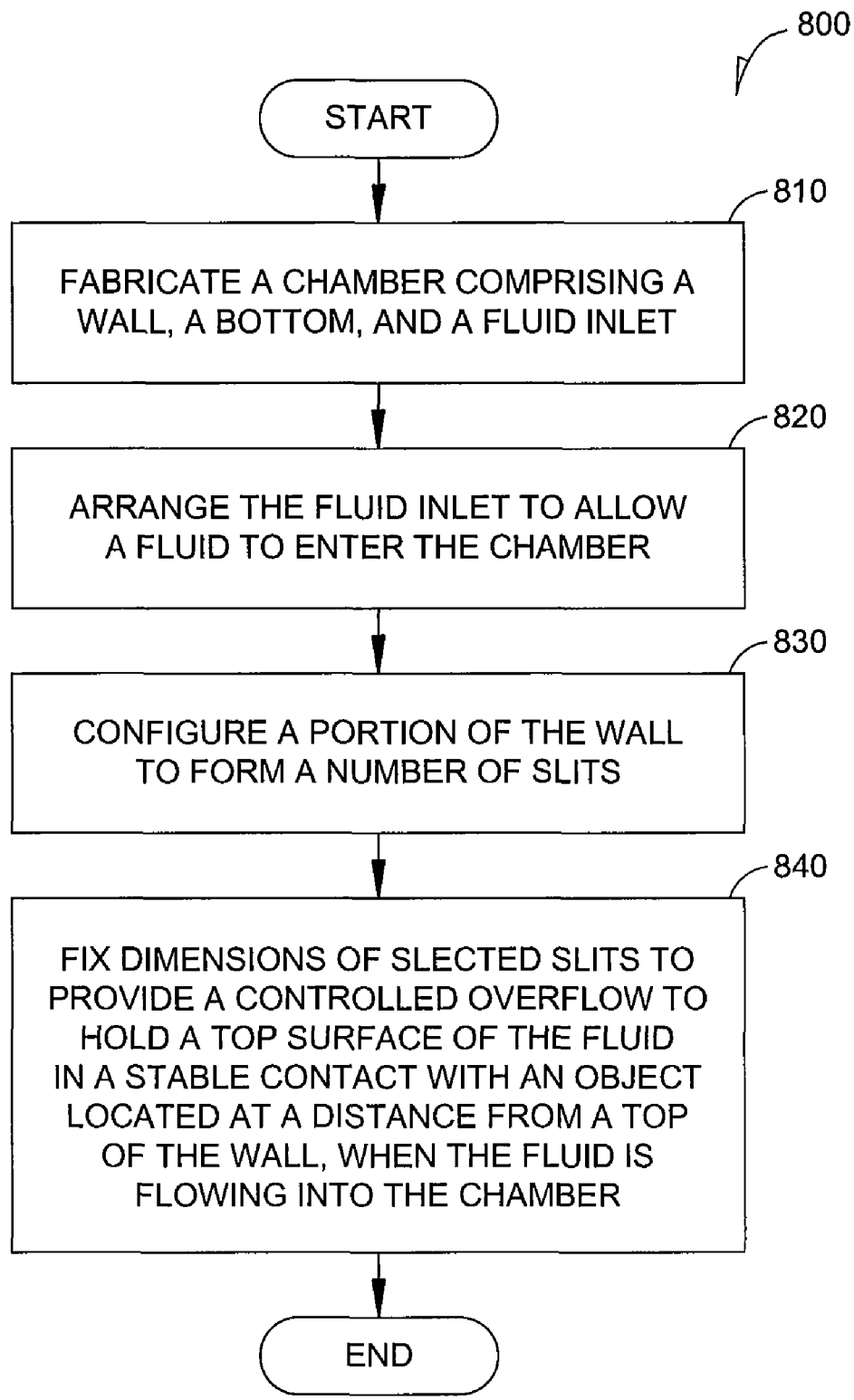
FIG. 8 is a flow diagram illustrating an example method for ultrasonic coupling using micro surface tension and capillary effects, according to various embodiments of the invention.

FIG. 8 is a flow diagram illustrating an example method 800 for ultrasonic coupling using micro surface tension and capillary effects, according to various embodiments of the invention. At operation 810, a chamber 210 including a wall, a bottom (e.g., the ultrasonic transducer 220 of FIG. 2), and a fluid inlet may be fabricated, procured, or otherwise provided. The fluid inlet, at operation 820, may be arranged to allow the coupling fluid 260 to enter the chamber 210. At operation 830, portions of the wall may be configured to form a number of slits 240 as shown in FIG. 3. The slits may allow the coupling fluid 260 of FIG. 2 to overflow to the outlet 250 while allowing the top surface of the coupling fluid 260 to remain in contact with the object 280 of FIG. 2.

At operation 840, the dimensions of selected ones of the slits 240 may be constructed to provide a controlled overflow to hold a top surface of the coupling fluid 260 in a stable contact with the object 280 located at a distance from a top of the wall, when the coupling fluid 260 is flowing into the chamber 210. In an embodiment, the dimensions of each of the slits 240 may be the same, but in other embodiments they may be different. The chamber 210 may be fabricated with the slits 240 to allow a coupling to be sustained between the coupling fluid 260 and the object 280 for a time period after an inflow from the fluid inlet is halted.

Figure 9:
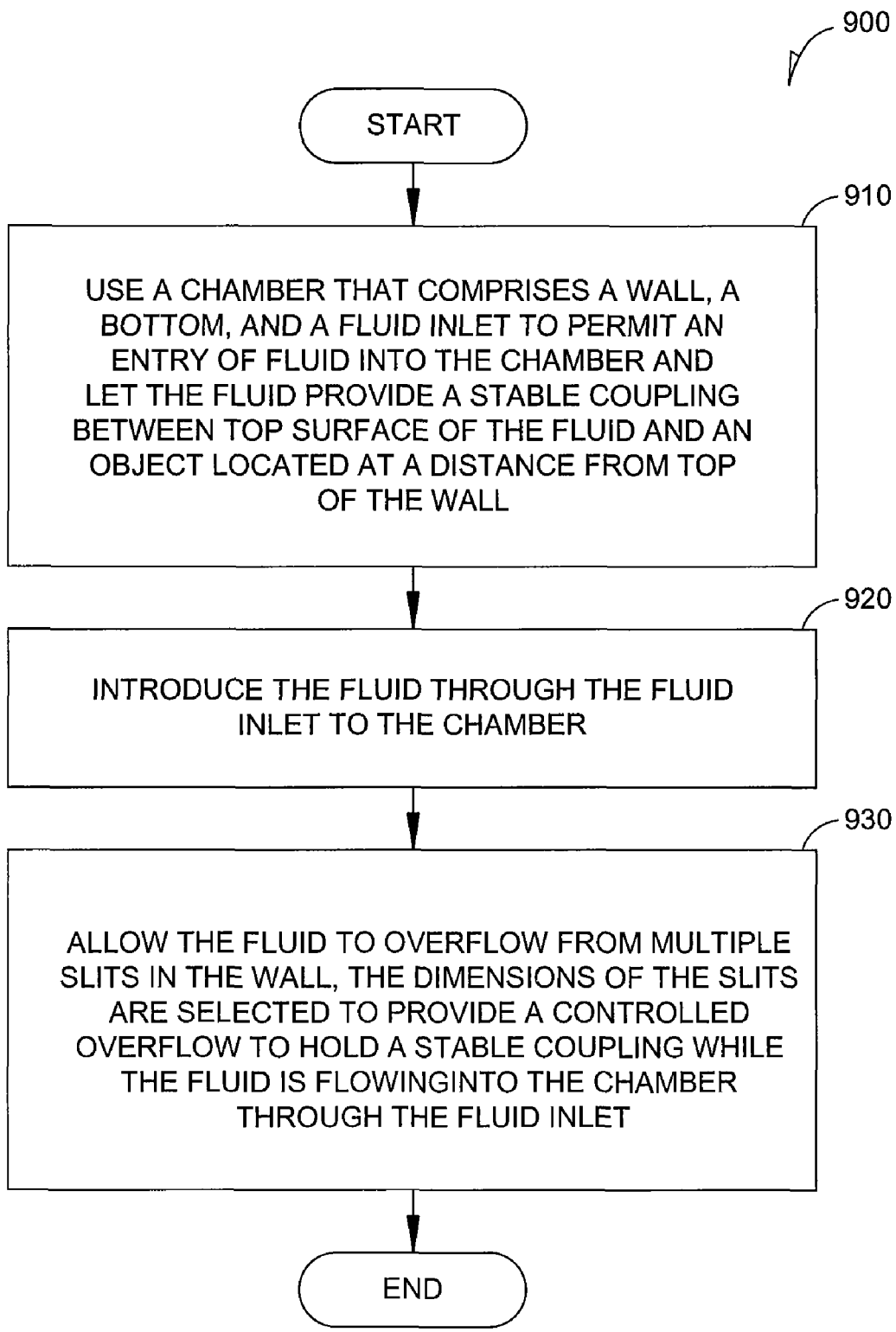
FIG. 9 is a diagram illustrating an example method of use of an apparatus for ultrasonic coupling using micro surface tension and capillary effects, according to various embodiments of the invention.

FIG. 9 is a diagram illustrating an example method 900 of use of the apparatus 200 for ultrasonic coupling using micro surface tension and capillary effects, according to various embodiments of the invention. At operation 910, the chamber 210 of FIG. 2 that comprises a wall, a bottom (e.g., the ultrasonic transducer 220 of FIG. 2), and a fluid inlet to permit an entry of the coupling fluid 260 into the chamber 210 may be used. The chamber 210 may be used, for example, in ultrasonic imaging of a sample including examining a sample surface and/or fluid mixing in biological and pharmaceutical applications.

The coupling fluid 260 may provide a stable coupling between a top surface of the coupling fluid 260 and the object 280 (FIGS. 2 and 5) located at a distance from top of the wall. The chamber may be used by introducing, at operation 920, the coupling fluid 260 through the fluid inlet 230 of FIG. 2 to the chamber 210 and, at operation 930, allowing the coupling fluid 260 to overflow from a number of slits 240 in the wall (as shown in FIG. 3). The dimensions of selected slits 240 may be adjusted or dimensioned to provide a controlled overflow to hold the stable coupling while the coupling fluid 260 is flowing into the chamber 210 through the fluid inlet. In an embodiment, the dimensions of each of the slits 240 may be the same, but in other embodiments they may be different. The method 900 may not be limited to the use of the apparatus 200 and may include using the apparatuses 200 or 600 of FIGS. 2 and 6, as described above, for example, in imaging and fluid mixing and other uses in biological, pharmaceutical and other applications. It should be noted that the operations described herein do not have to be performed in the order described, or in any particular order. Moreover, various activities described with respect to the operations identified herein can be performed in serial or parallel fashion. Although the flow diagrams of FIGS. 8 and 9 show an "End", the methods may be performed continuously if desired Embodiments of methods and apparatus for ultrasonic coupling between a coupling fluid and a sample object using micro surface tension and capillary effects have been described. Although the inventive subject matter has been described with reference to specific example embodiments, it will be evident that various modifications and changes may be made to these embodiments without departing from the broader spirit and scope of the inventive subject matter. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that allows the reader to quickly ascertain the nature of the technical disclosure. It is submitted with the understanding that it will not be used to interpret or limit the claims. In addition, in the foregoing Detailed Description, it may be seen that various features are grouped together in a single embodiment for the purpose of streamlining the disclosure. This method of disclosure is not to be interpreted as limiting the claims. Thus, the following claims are hereby incorporated into the Detailed Description, with each claim standing on its own as a separate embodiment.

What is claimed is:

1. An apparatus comprising:
    a chamber comprising a wall, a bottom, and a fluid inlet, the fluid inlet to allow a fluid to enter the chamber, a portion of the wall comprising a plurality of slits, selected ones of the plurality of slits having dimensions to allow a controlled overflow to hold a top surface of the fluid in a stable contact with an object located at a distance from a top of the wall, when the fluid is flowing into the chamber.

2. The apparatus of claim 1, wherein the chamber comprises a rectangular cylinder, and wherein the portion of the wall includes at least one side of the rectangular cylinder.

3. The apparatus of claim 1, wherein the plurality of slits have similar dimensions, and wherein the dimensions of each slit include a width and a height.

4. The apparatus of claim 3, wherein at least one of the width and the height of at least one of the plurality of slits is to provide sufficient surface tension to keep the fluid from escaping the chamber before the top surface of the fluid contacts the object.

5. The apparatus of claim 4, wherein at least one of the width and the height of at least one of the plurality of slits is to control the contacted area of the top surface of the fluid with the object.

6. The apparatus of claim 1, wherein the bottom comprises an ultrasonic transducer.

7. The apparatus of claim 6, wherein the ultrasonic transducer is an ultrasonic transducer array having a sensor plate formed to comprise a plurality of electrodes.

8. The apparatus of claim 7, wherein each of the plurality of electrodes is conductively coupled to a radio frequency source generating a signal having an impulse or a tone-burst waveform.

9. The apparatus of claim 8, wherein the radio frequency source is controlled to allow detection and dislodging of a bubble formed in the fluid.

10. The apparatus of claim 7, wherein each of the plurality of electrodes is configured to form a Fresnel lens to locally converge ultrasonic waves generated by the ultrasonic transducer array.

11. The apparatus of claim 1, wherein the object comprises a sample plate including a plurality of sample wells, each sample well to contain a sample.

12. The apparatus of claim 1, wherein the chamber is fabricated to sustain a coupling between the fluid and the object for a time period after an inflow from the fluid inlet is halted.

13. The apparatus of claim 12, wherein the inflow is controlled to sustain the coupling between the fluid and the object.

14. The apparatus of claim 12, wherein at least one of the plurality of slits comprises at least one of:
tapering, and
one or more coatings to influence surface tension.

15. A method comprising:
providing a chamber comprising a wall, a bottom, and a fluid inlet;
arranging the fluid inlet to allow a fluid to enter the chamber;
configuring a portion of the wall to form a plurality of slits;
fixing dimensions of selected ones of the plurality of slits to provide a controlled overflow to hold a top surface of the fluid in a stable contact with an object located at a distance from a top of the wall, when the fluid is flowing into the chamber.

16. The method of claim 15, wherein providing the chamber comprises providing a rectangular cylinder, and wherein the portion of the wall includes at least one side of the rectangular cylinder.

17. The method of claim 15, wherein fixing dimensions of selected ones of the plurality of slits comprises allowing selected ones of the plurality of slits to have similar dimensions, and wherein the dimensions of each slit include a width and a height.

18. The method of claim 17, further comprising fixing at least one of the width and the height of at least one of the plurality of slits to provide sufficient surface tension to keep the fluid from escaping the chamber before the top surface of the fluid contacts the object.

19. The method of claim 17, further comprising fixing at least one of the width and the height of at least one of the plurality of slits to control a contacted area of the top surface of the fluid with the object.

20. The method of claim 15, wherein the bottom comprises an ultrasonic transducer array formed by a sensor plate formed with a plurality of electrodes.

21. The method of claim 20, further comprising conductively coupling each of the plurality of electrodes to a radio frequency source to generate a signal having an impulse or a tone-burst waveform.

22. The method of claim 21, further comprising tuning the radio frequency source to allow detection and dislodging of a bubble formed in the fluid.

23. The method of claim 20, further comprising configuring each of the plurality of electrodes to form a Fresnel lens to locally converge ultrasonic waves generated by the transducer array.

24. The method of claim 15, further comprising sustaining a coupling between the fluid and the object for a time period after an inflow from the fluid inlet is halted.

25. The method of claim 24, further comprising controlling the inflow to sustain the coupling between the fluid and the object.

26. The method of claim 15, further comprising performing at least one of the following on at least one of the plurality of slits:
tapering, and
forming one or more coatings to influence surface tension.

27. A method comprising:
using a chamber that comprises a wall, a bottom, and a fluid inlet to permit an entry of fluid into the chamber, the fluid to provide a stable coupling between a top surface of the fluid and an object located at a distance from a top of the wall by:
introducing the fluid through the fluid inlet to the chamber;
allowing the fluid to overflow from a plurality of slits in a portion of the wall, the dimensions of selected ones of the plurality of slits adjusted to provide a controlled overflow to hold the stable coupling while the fluid is flowing into the chamber through the fluid inlet.

28. The method of claim 27, further comprising using the chamber to perform at least one of following acts:
ultrasonic imaging a sample including examining a sample surface; and
mixing fluid samples.

29. A system comprising:
a processor;
a memory coupled to the processor;
a radio frequency generator controlled by the processor to generate radio frequency waves; and
an ultrasonic transducer coupled to a sample plate via a fluid contained in a chamber, the chamber comprising a wall, a bottom, and a fluid inlet to allow the fluid to enter the chamber, a portion of the wall comprising a plurality of slits, dimensions of selected ones of the plurality of slits to provide a controlled overflow to hold a top surface of the fluid in a stable contact with an object located at a distance from a top of the wall, when the fluid is flowing into the chamber.

* * * * *

UNITED STATES PATENT AND TRADEMARK OFFICE
CERTIFICATE OF CORRECTION

PATENT NO. : 8,151,645 B2
APPLICATION NO. : 12/418505
DATED : April 10, 2012
INVENTOR(S) : Vibhu Vivek, Antonio Lucero and Michael Travis Page 1 of 1

It is certified that error appears in the above-identified patent and that said Letters Patent is hereby corrected as shown below:

On the Title Page, in column 1, under Item "(73) Assignee", line 1, delete "Microsoft" and insert --Microsonic--, therefor Signed and Sealed this
Twenty-fifth Day of November, 2014

Michelle K. Lee
*Deputy Director of the United States Patent and Trademark Office*